（12） United States Patent
Kawanishi et al.

(10) Patent No.: US 8,101,374 B2
(45) Date of Patent: Jan. 24, 2012

(54) OXIDATIVE CHROMOGENIC COMPOUND OR SALT THEREOF AND PRODUCTION METHOD THEREOF, AND REAGENT COMPOSITION AND TEST INSTRUMENT USING THE SAME

(75) Inventors: Tetsuro Kawanishi, Ashigarakami-gun (JP); Yuzuru Saito, Hadano (JP); Takako Ariga, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 333 days.

(21) Appl. No.: 12/528,112

(22) PCT Filed: Mar. 6, 2008

(86) PCT No.: PCT/JP2008/054090
§ 371 (c)(1),
(2), (4) Date: Aug. 21, 2009

(87) PCT Pub. No.: WO2008/114622
PCT Pub. Date: Sep. 25, 2008

(65) Prior Publication Data
US 2010/0062464 A1    Mar. 11, 2010

(30) Foreign Application Priority Data

Mar. 20, 2007 (JP) ................................ 2007-072807
Sep. 28, 2007 (JP) ................................ 2007-254475

(51) Int. Cl.
*C12Q 1/54* (2006.01)
*C12Q 1/28* (2006.01)
*C12N 9/02* (2006.01)
*C07D 231/22* (2006.01)
*C07D 231/24* (2006.01)

(52) U.S. Cl. .......... 435/14; 435/28; 435/190; 548/367.4
(58) Field of Classification Search .................. None
See application file for complete search history.

(56) References Cited

U.S. PATENT DOCUMENTS

| | | | |
|---|---|---|---|
| 3,079,256 A | 2/1963 | Van Poucke et al. | |
| 4,321,397 A | 3/1982 | Nix et al. | |
| 4,394,512 A | 7/1983 | Batz | |
| 4,452,188 A | 6/1984 | Kosuda et al. | |
| 4,567,139 A * | 1/1986 | Batz ................................ | 435/28 |
| 2005/0061289 A1 | 3/2005 | Plenzler et al. | |

FOREIGN PATENT DOCUMENTS

| | | |
|---|---|---|
| EP | 0 033 539 A1 | 8/1981 |
| JP | 2004-223115 A | 8/2004 |

OTHER PUBLICATIONS

Extended European Search Report issued by the European Patent Office on Jun. 7, 2010, in corresponding EP Application No. 08721510.9.

International Preliminary Report on Patentability issued by the International Bureau of WIPO on Sep. 22, 2009 in International Application No. PCT/JP2008/054090, and its English-language translation.
Search Report issued Oct. 28, 2009 in corresponding European Application No. 09 00 7753.8.
International Search Report (Form PCT/ISA/210) mailed Apr. 15, 2008.
Written Opinion of the International Searching Authority (PCT/ISA/237) mailed Apr. 15, 2008 (in Japanese).
K. Tamaoku et al., New Water-soluble Hydrogen Donors for the Enzymatic Photometric Determination of Hydrogen Peroxide. II. N-ethyl-N-(2-hydroxy-3-sulfopropyl) aniline derivatives, Chem. Pharm. Bull., 1982 (month unknown), vol. 30, No. 7, pp. 2492-2497.
V. Musil et al., "New Derivatives of 1,2-diphenyl-3,5-dioxopyrazolidine", Collection of Czechoslovak Chemical Communications, 1964 (month unknown), vol. 29, 1669-74 (abstract) Caplus; AN 1964:432389, DN 61:32389, RN:97235-63-7, compounds, 2 pages.
Official Action dated Jan. 26, 2011, issued by the Chinese Patent Office in corresponding Chinese Patent Application No. 200880008791.5, and partial English language translation of the Official Action.

* cited by examiner

*Primary Examiner* — Rebecca Anderson
*Assistant Examiner* — Alicia L Otton
(74) *Attorney, Agent, or Firm* — Buchanan Ingersoll & Rooney PC (57) ABSTRACT

It is an object of the present invention to provide a means for measuring a concentration of various components rapidly with high accuracy and high sensitivity. The present invention is to provide an oxidative chromogenic compound or salt thereof represented by the following chemical formula (1):

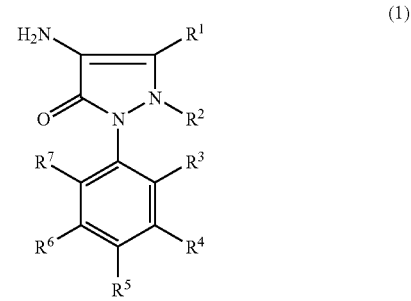

wherein $R^1$ and $R^2$ are each independently a linear or branched alkyl group having 1 to 5 carbon atoms;
$R^3$, $R^4$, $R^5$, $R^6$ and $R^7$ are each independently a hydrogen atom, a carboxyl group or a sulfonic acid group, or salt thereof, provided that at least one of $R^3$ to $R^7$ is a carboxyl group or a sulfonic acid group, or salt thereof, and the others are hydrogen atoms,
and the production method thereof, and the reagent composition and test instrument using the same.

21 Claims, 4 Drawing Sheets

OXIDATIVE CHROMOGENIC COMPOUND OR SALT THEREOF AND PRODUCTION METHOD THEREOF, AND REAGENT COMPOSITION AND TEST INSTRUMENT USING THE SAME

TECHNICAL FIELD

The present invention relates to an oxidative chromogenic compound and production method thereof, and a reagent composition and a test instrument using the same. In more detail, it relates to an oxidative chromogenic compound for the advantageous use in determination of a living body component and production method thereof, and a reagent composition and a test instrument using the same.

BACKGROUND ART

In these days, a colorimetric assay method using an enzyme has been widely used as one of methods for measuring a living body component in a body fluid (specimen) including blood or urine. These methods are introduced into a measuring kit, an automatic analyzer, and a Dry Chemistry test instrument etc., and used in a number of daily clinical examinations (for example, see JP-A-2004-223115).

As one of these measuring methods, there is a quantitation method which comprises having a specific oxidase (oxidative enzyme) acted on a substance to be measured to generate hydrogen peroxide, changing the hydrogen peroxide into active oxygen by peroxidase, oxidizing a coloring reagent with the active oxygen to generate a pigment, and colorimetrically determine the generated pigment.

As the enzyme to be used therein, for example, glucose oxidase has been used for measuring glucose, cholesterol oxidase has been used for measuring cholesterol, uricase has been used for measuring uric acid, and pyruvate oxidase has been used for measuring pyruvic acid. Since each of these enzymes specifically oxidizes only a substrate of the subject to be measured, only subject to be measured can be exclusively determined from a specimen including various components.

In addition, as the coloring reagent, pigments or precursors thereof (chromogen) has been used, in which absorption wavelength characteristics or absorption intensity thereof change by being oxidized with active oxygen. Specifically, amount of subject to be measured can be quantitatively determined by measuring color varying depending on the amount of active oxygen. These pigments and chromogen include those functioning in only one molecule form, and those functioning in a coupled form of different two molecules.

Among them, as the pigment functioning in one molecule form, leuco type pigment has been used. The compound includes benzidine, o-tolidine, o-dianisidine, 2,2'-amino-bis(3-ethylbenzothiazolinone-6-sulfonic acid) (ABTS), bis-(4-diethylamino)-2-sulfophenylmethane (BSPM), bis[3-bis(4-chlorophenyl)methyl-4-dimethylaminophenyl]amine (BCMA), 10-N-methylcarbamoyl-3,7-dimethylamino-10H-phenothiazine (MCDP), 3,3',5,5'-tetramethylbenzidine (TMBZ), bis[4-(N-alkyl-N-sulfopropyl)-2,6-dimethylphenyl]methane (Bis-MAPS), N,N,N',N',N'',N''-hexa(3-sulfopropyl)-4,4',4''-triaminotrip henylmethane (TMP), or the like.

Also, as a typical example using the pigment functioning in two molecules form, a method which comprises oxidatively coupling a coupler compound with Trinder's reagent has been known (for example, see: Trinder, P., Ann. Clin. Biochem., 6, 24, 1969, and Barham, D. and Trinder, P., Analyst (London), 97, 142, 1972).

As the coupler compound, 4-aminoantipyrine (4-AA), vanillin diamine sulfonic acid, methylbenzothiazolinone hydrazone (MBTH), sulfonated methylbenzothiazolinone hydrazone (SMBTH), aminodiphenylamine, or the derivatives thereof has been used.

As the Trinder's reagent, for example, phenol derivative or aniline derivative has been used. Examples of the phenol derivative include phenol, 4-chlorophenol, 2,4-dichlorophenol, 2,6-dichlorophenol, 3,5-dichlorophenol, 2,4-dibromophenol, 2,6,4-trichlorophenol, 2,6,4-tribromophenol, 3,5-dichloro-2-hydroxybenzene sulfonic acid, 3-hydroxy-2,4,6-triiodobenzoic acid, or the like. Examples of the aniline derivative include N-ethyl-N-(3-sulfopropyl)-3-methylaniline (TOPS), N-ethyl-N-(3-methylphenyl)-3-acetylethylenediamine (EMAE), N-ethyl-N-(3-methylphenyl)-N-succinylethylenediamine (EMSE), N-ethyl-N-(2-hydroxy-3-sulfopropyl)-3-methylaniline (TOOS), N-(2-carboxyethyl)-N-ethyl-3-methylaniline (CEMB), N,N-bis-(4-sulfobutyl)-3-methylaniline (TODB), N-ethyl-N-(2-succinylaminoethyl)-3-methylaniline (ESET), N-ethyl-N-(3-sulfopropyl)-3-methoxyaniline (ADPS), N-(2-hydroxy-3-sulfopropyl)-3,5-dimethoxyaniline (HSDA), N-ethyl-N-(2-hydroxy-3-sulfopropyl)-3,5-dimethoxyaniline (DAOS), N-ethyl-N-(2-hydroxy-3-sulfopropyl)-3,5-dimethoxy-4-fluoroaniline (FDAOS), N-ethyl-N-(2-hydroxy-3-sulfopropyl)-3,5-dimethylaniline (MAOS), or the like.

In practical products, a pigment functioning in two molecules form has a tendency to be employed much more, because a pigment functioning in one molecule form may have less stability when used in a reagent composition. In addition, among the pigments functioning in two molecules form, 4-aminoantipyrine (4-AA), which is most stable among the above-described compounds, has been frequently employed as a coupler compound, and aniline derivatives have been employed much more as a Trinder's reagent, because these compounds are more advantageous in respect to stability, coloring intensity and wave length, as compared with highly volatile phenol derivatives.

DISCLOSURE OF INVENTION

Recently, there has been increasing a need for technology measuring a glucose and cholesterol concentration in blood at high accuracy and within very short time, with increase of patients suffering from lifestyle-related diseases such as diabetes and hyperlipemia.

In view of these situations, in order to enhance the value of a test instrument using a coloring principle, it has been required to reduce time-dependent degradation of reagent, or further improve measurement accuracy. In addition, from the viewpoint of detecting a smaller amount of component, a detecting system with higher sensitivity as compared with existing systems will be required. In the field of a test instrument using a coloring principle, present situation is desired to develop a means for solving these problems.

It is an object of the present invention to provide a means for measuring a concentration (for example, blood concentration) of various components with a high accuracy and high speed, and high sensitivity.

The present inventors have investigated intensively for solving such problems, to find a novel coupler compound capable of solving such problems, and as a result, completed the present invention.

Specifically, the present invention is to provide an oxidative chromogenic compound and the production method thereof, and a reagent composition and a test instrument using the same as defined in the following (1) to (21).

(1) An oxidative chromogenic compound or salt thereof represented by the following chemical formula (1):

[Formula 1]

wherein $R^1$ and $R^2$ are each independently a linear or branched alkyl group having 1 to 5 carbon atoms;
$R^3$, $R^4$, $R^5$, $R^6$ and $R^7$ are each independently a hydrogen atom, a carboxyl group or a sulfonic acid group, or salt thereof, provided that at least one of $R^3$ to $R^7$ is a carboxyl group or a sulfonic acid group, or salt thereof, and the others are hydrogen atoms.

(2) The compound or a salt thereof according to the above item (1), wherein in the formula (1), $R^1$ and $R^2$ are a methyl group.

(3) The oxidative chromogenic compound or a salt thereof according to the above item (1) or (2), wherein in the formula (1), $R^5$ is a carboxyl group or a sulfonic acid group, or salt thereof, and $R^3$, $R^4$, $R^6$ and $R^7$ are a hydrogen atom.

(4) The oxidative chromogenic compound or a salt thereof according to the above item (1) or (2), wherein in the formula (1), $R^4$ is a carboxyl group or a sulfonic acid group, or salt thereof, and $R^3$, $R^5$, $R^6$ and $R^7$ are a hydrogen atom.

(5) The oxidative chromogenic compound or a salt thereof according to the above item (1) or (2), wherein in the formula (1), $R^4$ and $R^6$ are a carboxyl group or a sulfonic acid group, or salt thereof, and $R^3$, $R^5$ and $R^7$ are a hydrogen atom.

(6) A reagent composition comprising the oxidative chromogenic compound or salt thereof set forth in any one of the above items (1) to (5), a Trinder's reagent, oxidase, and peroxidase.

(7) The reagent composition according to the above item (6), wherein the Trinder's reagent is one or more members selected from the group consisting of:
N-ethyl-N-(3-sulfopropyl)-3-methylaniline;
N-ethyl-N-(3-methylphenyl)-3-acetylethylenediamine;
N-ethyl-N-(3-methylphenyl)-N-succinylethylenediamine;
N-ethyl-N-(2-hydroxy-3-sulfopropyl)-3-methylaniline;
N-(2-carboxyethyl)-N-ethyl-3-methylaniline;
N,N-bis-(4-sulfobutyl)-3-methylaniline;
N-ethyl-N-(2-succinylaminoethyl)-3-methylaniline;
N-ethyl-N-(3-sulfopropyl)-3-methoxyaniline;
N-(2-hydroxy-3-sulfopropyl)-3,5-dimethoxyaniline;
N-ethyl-N-(2-hydroxy-3-sulfopropyl)-3,5-dimethoxyaniline;
N-ethyl-N-(2-hydroxy-3-sulfopropyl)-3,5-dimethoxy-4-fluoroaniline; and
N-ethyl-N-(2-hydroxy-3-sulfopropyl)-3,5-dimethylaniline.

(8) The reagent composition according to the above item (6) or (7), which further comprises a pH buffer or a solubilizer.

(9) The reagent composition according to the above item (8), wherein the pH buffer is an organic acid salt.

(10) The reagent composition according to the above item (9), wherein the organic acid salt is an organic carboxylic acid salt.

(11) The reagent composition according to the above item (10), wherein the organic carboxylic acid salt is a salt of one or more acids selected from the group consisting of acetic acid, propionic acid, butyric acid, fumaric acid, maleic acid, phthalic acid, succinic acid, malonic acid, citric acid and malic acid.

(12) The reagent composition according to any one of the above items (8) to (11), wherein the pH of the pH buffer is in the range of 4.0 to 6.0.

(13) The reagent composition according to any one of the above items (8) to (12), wherein the solubilizer is one or more members selected from the group consisting of carboxymethylcellulose, polyethylene glycol, polyoxyethylene-p-t-octylphenol, sorbitan alkylate, sorbitan polyoxyethylene ether, polyoxylene-ethyleneoxyl block polymer, polyoxyethylene nonylphenol, and polyoxyethylene-n-alkyl ether.

(14) The reagent composition according to any one of the above items (6) to (13), wherein the molar ratio of contents of the oxidative chromogenic compound or salt thereof and the Trinder's reagent is 1:1 to 2:1.

(15) The reagent composition according to any one of the above items (6) to (14), wherein the oxidase is glucose oxidase.

(16) A test instrument having the reagent composition set forth in any one of the above items (6) to (15) supported on a carrier.

(17) The test instrument according to the above item (16), wherein the carrier is a polymeric membrane.

(18) The test instrument according to the above item (17), wherein the material constituting the polymeric membrane is polysulfone or polyether sulfone.

(19) The test instrument according to any one of the above items (16) to (18), wherein the content of the oxidative chromogenic compound or salt thereof is in the range of 15 to 62 µmol, the content of the Trinder's reagent is in the range of 7.5 to 62 µmol, the content of the pH buffer is in the range of 40 to 155 µmol, and the content of the solubilizer is in the range of 19 to 45 mg, per 1 cm$^3$ of the carrier.

(20) A process for the production of the oxidative chromogenic compound or salt thereof set forth in any one of the items (1) to (5), which comprises reacting a compound represented by the following chemical formula (2):

[Formula 2]

wherein $R^1$ is a linear or branched alkyl group having 1 to 5 carbon atoms,
with a compound represented by the following chemical formula (3):

[Formula 3]

(3)

wherein $R^3$, $R^4$, $R^5$, $R^6$ and $R^7$ are each independently a hydrogen atom, a carboxyl group or a sulfonic acid group, or salt thereof, provided that at least one of $R^3$ to $R^7$ is a carboxyl group or a sulfonic acid group, or salt thereof, and the others are hydrogen atoms.

(21) A process for the production of the oxidative chromogenic compound or salt thereof set forth in any one of the items (1) to (5), which comprises preparing as a starting material a compound represented by the following chemical formula (4):

[Formula 4]

(4)

wherein $R^1$ and $R^2$ are each independently a linear or branched alkyl group having 1 to 5 carbon atoms;

wherein $R^3$, $R^4$, $R^5$, $R^6$ and $R^7$ are each independently a hydrogen atom, a carboxyl group or a sulfonic acid group, or salt thereof, provided that at least one of $R^3$ to $R^7$ is a carboxyl group or a sulfonic acid group, or salt thereof, and the others are hydrogen atoms, and subjecting the compound to nitorosation reaction and followed by reduction reaction.

The oxidative chromogenic compound and the reagent composition of the present invention are superior to a conventionally known coloring compound or a reagent composition in points of the following (a) to (c).

(a) High solubility: In particular, in the case that the oxidative chromogenic compound is used by being supported on a membrane type carrier, the oxidative chromogenic compound, when a specimen is added (provided), can be quickly dissolved in the specimen to form a uniform solution and to give a color reaction, which permits quick and stable measurement. In addition, it is possible to avoid failures of correct measurements, which are based on precipitation of compounds by influence of other components in the reagent composition or components in the specimen.

In addition to the above mentioned advantage, a reagent solution with high concentration can be prepared, which contributes to improvement of sensitivity. As a result, when the reagent composition is used by being supported on a paper or a membrane type carrier, it is possible to support a larger amount of the reagent on the carrier by increasing the concentration of application liquid.

(b) Influences on measurement due to change in concentration of reagent are small: Specifically, influences on measurement are small, even when the oxidative chromogenic compound deteriorates with time, to decrease the amount thereof. In addition, when the oxidative chromogenic compound is used by being supported on a paper or a membrane type carrier, influences on measurement by variation of reagent concentration due to uneven application can be reduced.

(c) High sensitivity: When an object substance is to be detected and determined using the oxidative chromogenic compound or the reagent composition of the present invention, since absorbance can increase as compared with using a conventional coupler compound, improved measurement sensitivity can be expected.

Further other objects, characteristics, and features of the present invention will be apparent in consideration of the explanation cited hereinafter and the preferred embodiment exemplified by the accompanying drawings.

BEST MODE FOR CARRYING-OUT OF THE INVENTION

An embodiment of the present invention will be described in detail below.

[Oxidative Chromogenic Compound or Salt Thereof]

First aspect of the present invention is to provide an oxidative chromogenic compound or salt thereof (hereinafter, referred to simply as "oxidative chromogenic compound/salt") represented by the following chemical formula (1):

[Formula 5]

wherein $R^1$ and $R^2$ are each independently a linear or branched alkyl group having 1 to 5 carbon atoms;

$R^3$, $R^4$, $R^5$, $R^6$ and $R^7$ are each independently a hydrogen atom, a carboxyl group or a sulfonic acid group, or salt thereof, provided that at least one of $R^3$ to $R^7$ is a carboxyl group or a sulfonic acid group, or salt thereof, and the others are hydrogen atoms.

In the above chemical formula (1), $R^1$ and $R^2$ are each independently a linear or branched alkyl group having 1 to 5 carbon atoms. Preferably, $R^1$ and $R^2$ are the same alkyl group. As examples of the linear or branched alkyl group having 1 to 5 carbon atoms, methyl group, ethyl group, propyl group, isopropyl group, butyl group, isobutyl group, sec-butyl group, tert-butyl group, pentyl group, isopentyl group and neopentyl group may be cited, for example. Among them, considering from solubility of the oxidative chromogenic compound/salt represented by the chemical formula (1), $R^1$ and/or $R^2$ are more preferably methyl group, ethyl group, propyl group, and most preferably, both of $R^1$ and $R^2$ are a methyl group. By this embodiment, the oxidative chromogenic compound/salt represented by the chemical formula (1) can exhibit sufficient solubility in a solvent, and generation of coating unevenness can be prevented when supported on a carrier, and influences on measured values can be minimized even when concentrations of reagent are varied. In addition, the accuracy of measurement can be improved significantly when subjecting to oxidative chromogenic reaction with a suitable Trinder's reagent.

In the chemical formula (1), $R^3$ to $R^7$ is a hydrogen atom, a carboxyl group (—COOH) or a sulfonic acid group (—SO$_3$H), or a salt thereof. In this case, at least one group of $R^3$ to $R^7$ is a carboxyl group or a sulfonic acid group, or a salt thereof, and the remaining $R^3$ to $R^7$ are a hydrogen atom. It should be noted that $R^3$ to $R^7$ may be same or different each other. Among them, considering from the solubility of the oxidative chromogenic compound/salt represented by the chemical formula (1), the preferred embodiment is that $R^5$ is a carboxyl group or a sulfonic acid group, or a salt thereof, $R^3$, $R^4$, $R^6$ and $R^7$ are a hydrogen atom; $R^4$ is a carboxyl group or a sulfonic acid group, or a salt thereof, $R^3$, $R^5$, $R^6$ and $R^7$ are a hydrogen atom; or $R^4$ and $R^6$ are a carboxyl group or a sulfonic acid group, or a salt thereof, $R^3$, $R^5$ and $R^7$ are a hydrogen atom. According to such an embodiment, the oxidative chromogenic compound/salt represented by the chemical formula (1) can exhibit sufficient solubility in a solvent, and generation of coating unevenness can be prevented when supported on a carrier, and influences on measured values can be minimized even when concentrations of reagent are varied. In addition, the accuracy of measurement can be improved significantly when subjecting to oxidative chromogenic reaction with a suitable Trinder's reagent.

Specifically, preferable oxidative chromogenic compounds of the present invention are follows:

4-amino-1-(4-carboxyphenyl)-2,3-dimethyl-5-pyrazolone (in the chemical formula (1), $R^1$, $R^2$=—CH$_3$; $R^5$=—COOH; $R^3$, $R^4$, $R^6$, $R^7$=H);

4-amino-1-(4-sulfophenyl)-2,3-dimethyl-5-pyrazolone (in the chemical formula (1), $R^1$, $R^2$=—CH$_3$; $R^5$=—SO$_3$H; $R^3$, $R^4$, $R^6$, $R^7$=H);

4-amino-1-(3-carboxyphenyl)-2,3-dimethyl-5-pyrazolone (in the chemical formula (1), $R^1$, $R^2$=—CH$_3$; $R^4$=—COOH; $R^3$, $R^5$, $R^6$, $R^7$=H);

4-amino-1-(3-sulfophenyl)-2,3-dimethyl-5-pyrazolone (in the chemical formula (1), $R^1$, $R^2$=—CH$_3$; $R^4$=—SO$_3$H; $R^3$, $R^5$, $R^6$, $R^7$=H);

4-amino-1-(3,5-dicarboxyphenyl)-2,3-dimethyl-5-pyrazolo (in the chemical formula (1), $R^1$, $R^2$=—CH$_3$; $R^4$, $R^6$=—COOH; $R^3$, $R^5$, $R^7$=H);

4-amino-1-(3,5-disulfophenyl)-2,3-dimethyl-5-pyrazolone (in the chemical formula (1), $R^1$, $R^2$=—CH$_3$; $R^4$, $R^6$=—SO$_3$H; $R^3$, $R^5$, $R^7$=H);

4-amino-1-(3-carboxy-5-sulfophenyl)-2,3-dimethyl-5-pyrazolone (in the chemical formula (1), $R^1$, $R^2$=—CH$_3$; $R^4$=—COOH, $R^6$=—SO$_3$H; $R^3$, $R^5$, $R^7$=H).

Among them, more preferable oxidative chromogenic compounds of the present invention are follows:

4-amino-1-(4-carboxyphenyl)-2,3-dimethyl-5-pyrazolone (in the chemical formula (1), $R^1$, $R^2$=—CH$_3$; $R^5$=—COOH; $R^3$, $R^4$, $R^6$, $R^7$=H);

4-amino-1-(4-sulfophenyl)-2,3-dimethyl-5-pyrazolone (in the chemical formula (1), $R^1$, $R^2$=—CH$_3$; $R^5$=—SO$_3$H; $R^3$, $R^4$, $R^6$, $R^7$=H);

4-amino-1-(3-carboxyphenyl)-2,3-dimethyl-5-pyrazolone (in the chemical formula (1), $R^1$, $R^2$=—CH$_3$; $R^4$=—COON; $R^3$, $R^5$, $R^6$, $R^7$=H);

4-amino-1-(3-sulfophenyl)-2,3-dimethyl-5-pyrazolone (in the formula (1), $R^1$, $R^2$=—CH$_3$; $R^4$=—SO$_3$H; $R^3$, $R^5$, $R^6$, $R^7$=H).

It should be note that although a carboxyl group and a sulfonic acid group are an ionic functional group, these functional groups may be in a free state or in the form of a salt, that is, $R^3$, $R^4$, $R^5$, $R^6$ and $R^7$ may be a salt of a carboxyl group or a sulfonic acid group. In this case, a counter ion which forms a salt with these acid groups may be an inorganic ion or an organic ion. For example, cation derived from inorganic base, such as sodium ion, potassium ion, calcium ion; ammonium ion; cation derived from organic base such as alkylamines; and ion derived from amphoteric compound such as amino acids may be included. Among them, when the oxidative chromogenic compound represented by the chemical formula (1) is in the form of a salt, sodium salt, potassium salt, or ammonium salt is preferable, and sodium salt is more preferable. The oxidative chromogenic compound/salt may be included singly or in a mixture of two or more members in the reagent composition of the present invention.

A process for the production of the oxidative chromogenic compound/salt of the present invention is not particularly limited, and the conventionally known methods can be applied in the same manner, or by the appropriate modification or by the appropriate combination thereof. Hereinafter, a preferred embodiment of the process for producing the oxidative chromogenic compound/salt of the present invention is described, but the technical scope of the present invention should not be limited to the following embodiment.

The oxidative chromogenic compound/salt of the present invention, for example, may be preferably produced by the process comprising a step (hereinafter, referred to as "step

A") of reacting a compound represented by the following chemical formula (2) (hereinafter, referred to as "compound (2)"):

[Formula 6]

(2)

with a compound represented by the following chemical formula (3) (hereinafter, referred to as "compound (3)").

[Formula 7]

(3)

$R^1$ and $R^3$ to $R^7$ in the chemical formulae (2) and (3) are defined as in the chemical formula (1), and therefore, the detailed description thereof is omitted herein.

In the step (A), mixing ratio when reacting the compound (2) with the compound (3) is not particularly limited. Preferably, the compound (2) and the compound (3) may be mixed in an equimolar ratio, or the compound (2) may be mixed in a slightly larger amount than that of the compound (3). Specifically, an amount of the compound (2) to be mixed is preferably in the range of 0.8 to 2 moles, more preferably in the range of 1 to 1.2 moles, based on 1 mole of the compound (3). In addition, reaction conditions of the compound (2) with the compound (3) are not particularly limited as long as these reactions proceed. For example, reaction temperature is preferably in the range of 20 to 200° C., more preferably in the range of 80 to 150° C. In addition, reaction time is preferably in the range of 0.5 to 5 hours, more preferably in the range of 1 to 1.5 hours. Further, the reaction of the compound (2) with the compound (3) may be carried out in the absence of a solvent or in a solvent. In the latter case, the solvent used therein may include alcohols such as methanol, ethanol, propanol; ethers such as tetrahydrofuran (THF), diethyl ether, dioxane; solvents such as pyridine, dimethylformamide, dimethylsulfoxide. Among them, THF is preferably used. After the reaction of compound (2) with the compound (3), the reaction mixture may be added to a suitable solvent to solidify the product, and then the product may be separated from raw materials and recovered. The reaction product obtained from the step (A) have a structure of the following chemical formula (4) wherein $R^2$ is a hydrogen atom (H).

Subsequently, by alkylating the reaction product obtained from the step (A), the compound represented by the following chemical formula (4) (hereinafter, referred to as "compound (4)"):

[Formula 8]

(4)

can be obtained (step (B)).

In the step (B), the alkylation reaction can be carried out by using an alkylation agent including alkyl halide such as methyl iodide, ethyl iodide. But the alkylation agent is not limited to the alkyl halide, and another conventionally known alkylation agent can be used instead. In the reaction of step (B), an appropriate solvent or a base may be used. In addition, the reaction may be carried out at room temperature or under heating conditions. Specifically, as the solvent to be used, the same solvent as those enumerated in the step (A) may be included. Among them, methanol or THF is preferably used. In addition, as the base, triethylamine (TEA), diisopropylethylamine (DIEA), 4-(dimethylamino) pyridine etc. may be included. Among them, TEA is preferably used.

In the step (B), the amount used of alkylating agent is not particularly limited, as long as it is sufficient for capable of alkylating the reaction product obtained in the step (A). For example, the amount of alkylating agent used is preferably in the range of 0.5 to 5 moles, more preferably in the range of 1 to 2 moles, based on 1 mole of the reaction product to be obtained in the step (A). In addition, reaction conditions are not particularly limited. Alkylation of the reaction product obtained in the step (A) is preferably carried out at 40 to 200° C., more preferably at 100 to 140° C., and preferably for 1 to 24 hours, more preferably for 10 to 20 hours.

Subsequently, the compound (4) obtained in the step (B) as a starting material can be subjected to nitrosation reaction, followed by reduction reaction (step (C)).

In the step (C), although nitrosation reaction may be carried out in a solution-free condition, it is preferably carried out in a solvent. Specifically, nitorosation reaction may be carried out by using as a solvent a water, an organic acid, or the mixture of them, acidifying the reaction system by adding hydrochloric acid or nitric acid (preferably hydrochloric acid), preferably to give pH 1 to 5, more preferably pH 1 to 2, and then adding a sodium nitrite. The organic acid may include acetic acid, propionic acid, butyric acid, formic acid, lactic acid, succinic acid, and citric acid etc. Acetic acid is preferable. Although the amount of sodium nitrite is not particularly limited, it is generally used in an equimolar or excess amount relative to the starting material, preferably in an amount of 1.0 to 4.0 equivalents, more preferably 1.1 to 1.5 equivalents, based on the starting material.

In the step (C), reaction conditions of nitorosation reaction is not particularly limited as long as the nitorosation reaction can be carried out sufficiently. Specifically, the reaction temperature is preferably in the range of −20° C. to 40° C., more preferably in the range of 0 to 25° C. Also, the reaction time is preferably in the range of 5 seconds to 40 minutes, more preferably in the range of 10 seconds to 15 minutes. Since the product obtained by the nitorosation reaction may be precipitated, it can be easily recovered by separation from the reaction system.

Next, in the step (C), the reduction reaction may be carried out following the nitorosation reaction. Although the reduction reaction may be carried out in the absence of a solvent, it is preferably carried out in a solvent. The solvent, which can be used in the reduction reaction, is not particularly limited, as long as the nitrosation reaction product obtained by nitorosation reaction can be dissolved. Such a solvent may include, for example, water; alcohols such as methanol, ethanol, propanol; and organic acids such as acetic acid, propionic acid, butyric acid, formic acid, lactic acid, succinic acid, citric acid. These solvents may be used singly or as a mixture of two or more members. Although the reducing agent used therein is not particularly limited, metals such as zinc; reductive inorganic salts such as sodium hydrosulfite may be used, for example. The reaction solution may be appropriately adjusted to a neutral, or basic or acidic level by addition of sodium hydroxide or hydrochloric acid. Preferably, the pH of reaction solution is in the range of 1 to 12, more preferably 1 to 5.

After the reduction reaction, the product may be precipitated by adding an appropriate solvent, and recovered by filtration or extraction using an appropriate organic solvent. The nitorosation reaction and the reduction reaction may be successively carried out in one pot without taking out the product by nitorosation reaction. The recovered product may be obtained in a purer state by purification with recrystallization or column chromatography.

The production process mentioned above may optionally include a step of introducing a suitable protecting group before the reaction step, and then deprotecting it. The protecting group for carboxylic acid may include, for example, methyl ester or ethyl ester etc.

As above, embodiments of the preferable process for producing the oxidative chromogenic compound/salt of the present invention have been described, but the present invention should not be limited by such a method.

The second aspect of the present invention is to provide a reagent composition comprising the oxidative chromogenic compound or salt thereof of the first aspect of the present invention, a Trinder's reagent, oxidase, and peroxidase.

Specific embodiment of the oxidative chromogenic compound/salt to be included in the reagent composition of the present invention is defined as above, so the detailed description is omitted.

The content of the oxidative chromogenic compound/salt included in the reagent composition of the present invention is not particularly limited. As a preferable example, when the reagent composition is liquid form, concentration of the oxidative chromogenic compound/salt in a solution may be preferably in the range of 7 to 30 mmol/100 mL, more preferably 10 to 18 mmol/100 mL.

Hereinafter, ingredients other than the oxidative chromogenic compound/salt to be included in the reagent composition of the present invention will be specifically described. But the technical scope of the present invention should not be limited only to the following embodiment.

[Trinder's Reagent]

Specific embodiment of the Trinder's reagent is not particularly limited. Conventionally known knowledge can be appropriately referred. For example, it may include N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(3-sulfopropyl)-3-methylaniline, N-ethyl-N-(3-methylphenyl)-3-acetylethylenediamine, N-ethyl-N-(3-methylphenyl)-N-succinylethylenediamine, N-(2-carboxyethyl)-N-ethyl-3-methylaniline, N,N-bis-(4-sulfobutyl)-3-methylaniline, N-ethyl-N-(2-succinylaminoethyl)-3-methylaniline, N-ethyl-N-(3-sulfopropyl)-3-methoxyaniline, N-(2-hydroxy-3-sulfopropyl)-3,5-dimethoxyaniline, N-ethyl-N-(2-hydroxy-3-sulfopropyl)-3,5-dimethoxyaniline, N-ethyl-N-(2-hydroxy-3-sulfopropyl)-3,5-dimethoxy-4-fluoroaniline etc. When the Trinder's reagent is used in the reagent composition in combination with the oxidative chromogenic compound/salt, absorption when emitting at measurement can increase as compared with the case of using a conventional coupler compound such as 4-aminoantipyrine. Accordingly, sensitivity of measurement can be improved. Among them, from the viewpoint of improved slope of standard curve (i.e., improved sensitivity of measurement), N-ethyl-N-(2-hydroxy-3-sulfopropyl)-3-methylaniline (TOOS) and N-ethyl-N-(2-hydroxy-3-sulfopropyl)-3,5-dimethylaniline (MAOS) are particularly preferable. Trinder's reagent may be included singly or in a mixture of two or more members in the reagent of the present invention.

When the reagent composition of the present invention is used as a reagent for detecting and quantifying an object substance, the oxidative chromogenic compound/salt may bind to a Trinder's reagent at 1:1 (molar ratio), to form a pigment, and lead to give a color. Therefore, the ratio of contents between oxidative chromogenic compound/salt and Trinder's reagent is in theory 1:1 (molar ratio). However, because these reagents are practically affected by their solubility and reactivity, from the viewpoint of efficiently proceeding the reaction, the ratio of contents between the oxidative chromogenic compound/salt and the Trinder's reagent in the reagent composition of the present invention, as a molar ratio, is preferably 1:1 to 2:1, and more preferably 1.3:1.

[Oxidase]

The oxidase serves to specifically oxidize an object substance to be detected and quantified by utilizing the reagent composition of the present invention, to generate hydrogen peroxide. A specific embodiment of oxidase is not particularly limited, and the conventional known knowledge can be referred to as appropriate. That is, the kind of oxidase may be selected appropriately, depending on the kind of the object substance to be desired to detect and quantify using the reagent composition of the present invention. For example, glucose oxidase can be used for detecting and quantifying glucose; cholesterol oxidase can be used for detecting and quantifying colesterol; uricase can be used for detecting and quantifying uric acid; and pyruvate oxidase can be used for detecting and quantifying pyruvic acid. However, the present invention should not be limited only to these oxidases, and another oxidase may be used. Although the content of oxidase in the reagent composition of the present invention is particularly limited, from the viewpoint of efficiently proceeding reaction, the content is preferably in the range of 26 to 130 kU, and more preferably 26 to 108 kU, based on the content of oxidative chromogenic compound/salt (one mole). It should be noted that, in the present invention, the value of the oxidase content is determined by a colorimetric activity measuring method.

[Peroxidase]

Peroxidase acts on hydrogen peroxide generated by the oxidation of object substance to be detected and quantified, to generate active oxygen. A specific embodiment of peroxidase is not particularly limited, and the conventional known knowledge can be referred to as appropriate. Although the content of peroxidase in the reagent composition of the present invention is not particularly limited, from the viewpoint of efficiently proceeding reaction, the content is preferably in the range of 69 to 470 kU, and more preferably 69 to 350 kU, based on the content of oxidative chromogenic compound/salt (one mole). It should be noted that, the value of the peroxidase content is determined by a colorimetric activity measuring method.

[Other Components]

The reagent composition of the present invention may optionally include another component, in addition to the essential components as mentioned above. Another component, which can be optionally included in the reagent composition, for example, may include a pH buffer, a solubilizer, an osmoregulator, a surfactant, a stabilizing agent and a protecting agent, etc. A specific embodiment of each of these components is not particularly limited, and the conventional known knowledge can be referred to as appropriate. In particular, it is preferable to further include at least either of a pH buffer or a solubilzer.

The pH buffer may be incorporated in order to minimize pH variation when the reagent composition contacts with a specimen at detecting and quantifying an object substance, to maintain pH of a reaction system at a constant level even if any specimen is provided to a test instrument. As a result, it permits to proceed reaction always under the same conditions, and to improve measurement accuracy. As examples of the pH buffer, inorganic acid salts such as phosphate and borate, and organic acid salts such as organic carboxylate, organic phosphate, organic sulfonate, organic borate, amino acid and the salts thereof may be cited. Among them, from the viewpoint of improving stability and coloring performance of the reagent, organic acid salts are preferable, and organic carboxylate is more preferable. Examples of the organic carboxylate as a pH buffer may include, for example, salts of one or more acids selected from the group consisting of acetic acid, propionic acid, butyric acid, fumaric acid, maleic acid, phthalic acid, oxalic acid, succinic acid, malonic acid, citric acid, malic acid, pyruvic acid, glyceric acid, and glutaric acid. Among them, from the viewpoint of improving stability and coloring performance of the reagent, phthalic acid, succinic acid, citric acid, malonic acid, oxalic acid, fumaric acid and maleic acid are preferable, and succinic acid and citric acid are particularly preferable. When the pH buffer is in the form of a salt, a counter ion forming the salt together with an acid, for example, may include lithium ion, sodium ion, potassium ion, magnesium ion, calcium ion, ammonium ion, and alkyl ammonium ions. Among them, sodium ion and potassium ion are particularly preferable. The pH buffer may be used singly or in a mixture of two or more members in the reagent composition.

In the reaction of an enzyme for measurement or of a process forming a pigment, the reaction rate thereof may be frequently dependent on pH. Therefore, it will be possible to improve the reaction rate by setting the pH of the reaction system to an optimum pH of the enzyme in the reagent composition. In addition, in some cases, the reaction rate may be improved by setting the pH to a pH suitable for a coloring reaction in a reaction system. Furthermore, setting to an appropriate pH may improve solubility of a reagent component, leading to an improved reaction rate. In addition, setting to an appropriate pH may improve preservation stability of reagent components. From these points, the pH of the pH buffer is not particularly limited, and can be set appropriately depending on another component of the reagent composition. From viewpoint of superior reaction rate in coloring, the pH of pH buffer is preferably in the range of 4.0 to 6.0, and more preferably 4.0 to 5.0. In addition, in a preferred embodiment, the content of pH buffer in the reagent composition preferably is in the range of 1 to 6.7 moles, and more preferably 1.9 to 5 moles, based on the content of oxidative chromogenic compound/salt (one mole).

The solubilizer may be incorporated in order to uniformly mix a specimen with the reagent composition and to promptly proceed reaction, when the specimen is contacted with the reagent composition at the time of detecting and quantifying an object substance. When the reagent composition of the present invention is used, for example, in the form of a test instrument including the reagent composition supported on a carrier, it serves to improve wettability of the carrier surface, and to develop evenly the specimen on the carrier surface. Further, it can contribute to perform evenly and promptly a process in which the specimen penetrates into the inside of carrier with mixing and reacting with the reagent composition. In addition, the solubilizer has effects of wrapping the reagent composition to reduce a surface area contacting with air, and also has a function of preventing the degradation with time of unstable component for oxidation etc. Furthermore, when a protein such as enzyme is in a dry state, the solubilizer has a function of preventing the deterioration by stabilizing a higher-order structure of the protein. As the solubilizer, for example, a water-soluble polymer and a surfactant may be used. Specifically, carboxymethyl cellulose (CMC), polyethylene glycol (PEG), polyoxyethylene-p-t-octyl phenol (for example, Triton (registered trademark) series, manufactured by Union Carbide Chemicals and Plastics Co.), sorbitan alkylate (for example, Span (registered trademark) series, manufactured by ICI Americans, Inc), sorbitan polyoxyethylene ether (for example, Tween series, manufactured by Uniqema), polyoxylene-ethyleneoxyl blockpolymer (for example, Pluronic (registered trademark) series, manufactured by BASF AG.), polyoxyethylene nonyl phenol (for example, Nikkol NP series, manufactured by Nikko Chemicals), and polyoxyethylene-n-alkyl ether (for example, Brij (registered trademark) series, manufactured by ICI Americans, Inc.) may be included. Among them, CMC, PEG-5000 to 60000, Triton (registered trademark), Tween, Pluronic (register trademark), NP-40, Brij (registered trademark)-58 are preferable, and Triton (registered trademark) X-100, Tween 20, Pluronic (registered trademark)-F68 are particularly preferable. In a preferred embodiment, the content of the solubilizer in the reagent composition is preferably in the range of 480 to 2000 g, and more preferably 600 to 1300 g, based on the content of oxidative chromogenic compound/salt (one mole).

As a component which can be incorporated in the reagent composition of the present invention, an osmo-regulator, a stabilizing agent, a protective agent etc. may be selected, if necessary.

The form of the reagent composition of the present invention is not particularly limited. The reagent composition may be in any form such as liquid form, powdery form, and tablet form. The reagent composition of the present invention is preferably used in a form supported on a carrier. To be specific, the third aspect of the present invention is to provide a test instrument that the reagent composition according to the second aspect of the present invention is supported on a carrier. In such a form, the test instrument according to the third aspect of the present invention may comprise, for example, a layer in which the reagent composition according to the second aspect of the present invention is supported. In addition to this layer, the test instrument may further comprise another layer such as a measuring layer, a developing layer, a filtering layer, and a holding layer, if necessary. As for detection and quantification of an object substance using such test instrument, a method which comprises visually determining change of color after providing a specimen, or a method which comprises measuring reflection-absorbance using a spectrophotometer may be employed. As for measured values, they may be converted into an amount of measuring object (object substance) by comparison with the pre-created standard curve.

Hereinafter, the typical embodiment of the third aspect of the present invention will be explained in detail, but the technical scope of the present invention should not be limited to only the following embodiments. For example, when the reagent composition according to the second aspect of the present invention is used in the form of a liquid as mentioned above, the reagent composition may be mixed and reacted with the specimen, and thereafter the change in color may be visually determined, or the transmission-absorbance may be measured using a spectrophotometer.

When the reagent composition is used by being supported on a carrier, known methods can be employed, such as a method which comprises coating a solution having the reagent composition dissolved in an appropriate solvent on a carrier, and a method which comprises casting a matrix precursor including the reagent composition to form a test layer.

As a material constituting the carrier, porous materials such as papers, fabrics, and polymer membranes can be employed. Among them, from the viewpoint of superior coloring performance, it is particularly preferable to use polymer membranes as a material of the carrier. It should be noted that a "polymer membrane" means a water-insoluble porous membrane consisting of a polymer. Although there are no particular limitations on a polymer constituting the polymer membrane, for example, polysulfone, polyethersulfone, cellulous, cellulose acetate, cellulose nitrate, polyacrylonitrile, polyamide, aromatic polyamide, polycarbonate, polyethylene terephthalate, polyimide, polyethylene, polypropylene, polytetrafluoroethylene, polyvinyidene fluoride, polyvinyl chloride, and polyvinyl alcohol etc. may be cited. Among them, from the viewpoint of superior coloring performance, polysufone and polyethersulfone are preferably employed. As a method for producing the polymer membrane by forming the membrane from the polymer, methods which have been generally known in the art can be applied.

For coating the reagent composition on the carrier, the coating methods which have been generally employed in industries can be used.

In the test instrument of the present invention, the reagent composition according to the second aspect of the present invention may be supported on the carrier. The amount of each component supported on the carrier is not particularly limited, and can be selected appropriately by taking account of viscosity etc. of a solution. As one preferred example where the reagent composition supported on the carrier includes a pH buffer and a solubilizer, the amount of the oxidative chromogenic compound/salt to be supported is preferably in the range of 15 to 62 μmol per 1 $cm^3$ of the carrier, and more preferably 23 to 39 μmol per 1 $cm^3$ of the carrier. The amount of Trinder's reagent to be supported is preferably in the range of 7.5 to 62 μmol, and more preferably 15 to 39 μmol, per 1 $cm^3$ of the carrier. When the reagent composition supported on the carrier includes a pH buffer, the amount of the pH buffer to be supported is preferably in the range of 40 to 155 μmol, and more preferably 76 to 115 μmol, per 1 $cm^3$ of the carrier. When the reagent composition supported on the carrier includes a solubilizer, the amount of the solubilizer to be supported is preferably in the range of 19 to 45 mg, and more preferably 24 to 30 mg, per 1 $cm^3$ of the carrier.

For reducing a liquid transfer and an uneven drying after coating, a fine printing technique which comprises exactly weighing small amount of liquid and coating the liquid may be suitably used, but this technique requires essentially preparing a coating liquid of a high reagent concentration. In this point, the existing coupler compound such as 4-aminoantipyrine shows the lowest solubility among variety of reagents employed for measurement, and this causes a problem in preparing a coating liquid having a high concentration. In contrast, the coupler compound included in the reagent composition of the present invention shows high solubility and is desirable at the viewpoint of producing a coating liquid having a high concentration.

In the test instrument according to the third aspect of the present invention, in which the reagent composition according to the second aspect of the present invention is supported on a carrier, each component contained in the reagent composition is firstly dissolved into liquid component of the specimen after providing a specimen, and mixed to carry out the reaction. Then, quantification is carried out by a step which comprises generating a coloring compound to be usually transferred to a reading surface located on the opposite side of the surface provided with specimen of the test instrument, and measuring color tone change on the reading surface. Therefore, high solubility of the reagent component not only has advantages in uniform dissolution by a specimen, homogenization and rapid reaction, but also has advantages in smooth and uniform transfer to the reading surface because a pigment generated has superior solubility. These features contribute to shortened measuring time, improved measurement accuracy, and reduced variation in measured values.

When the test instrument has a reagent composition including 4-aminoantipyrine, a conventional coupler compound, supported on a carrier, the reagent component is deteriorated and reduced with time, and in association with the phenomenon problems arise such that the measured values increase. As for the reason of increase of the measured values accompanied by decrease of the reagent component, it is considered that the reason is not inhibition of enzyme reaction and coloring reaction, but any obstructions may be given to solubility and transfer of other reagents or fluidity in generated pigments at a higher concentration of the compound. According to the present invention, the influences on measured values can be reduced even if the amount increases or decreases, as compared with the case of using the conventional 4-aminoantipyrine, and the problems appeared in using 4-aminoantipyrine can be improved.

In addition, the conventional coupler compound such as 4-aminoantipyrine has a problem in which change in concentrations affects on measured values when a test instrument having a carrier on which the compound is supported is used. It has been suggested that when uneven coating is generated during coating on a bulk carrier, sensitivity differences arise between test instruments obtained by cutting carriers out. Alternatively, when the compound is degraded during storage to change the amount, measured value is affected. On the contrary, according to the present invention, it has an advantage that influences on measured values by changes of concentration are smaller, as compared with conventional 4-aminoantipyrine, and the problems can be improved.

EXAMPLES

The present invention will be described in more detail by referring to the following examples. The technical scope of the present invention, however, should not be limited to only the following examples.

Example 1

Synthesis of 4-amino-1-(4-carboxyphenyl)-2,3-dimethyl-5-pyrazolone (referred to as CP1)

1-1) Synthesis of 1-(4-carboxyphenyl)-3-methyl-5-pyrazolone

A mixture of 5.0 g of phenylhydrazine-4-carboxylic acid (manufactured by KANTO CHEMICAL Co., Inc.: 41179-1A) and 5.9 g of ethyl 3-oxobutanoate (manufactured by TOKYO CHEMICAL INDUSTRY Co., Ltd.: A0649) was stirred for 1 hour at 120° C. under heating. After cooling, a precipitated solid was collected by filtration, washed with ethanol, and then dried to yield 8.3 g of a desired product.

1-2) Synthesis of 1-(4-carboxyphenyl)-2,3-dimethyl-5-pyrazolone methyl ester 3.0 g of 1-(4-carboxyphenyl)-3-methyl-5-pyrazolone obtained in the above 1-1), 3.9 g of methyl iodide (manufactured by KANTO CHEMICAL Co., Inc.: 10060), and 100 mL of methanol were put in a high-pressure reactor, and stirred for 15 hours at 120° C. under heating. The reaction mixture was evaporated to dryness, dissolved in chloroform, washed with water. Subsequently, an organic layer was dried with anhydrous sodium sulfate. The organic layer was evaporated to dryness to yield 2.6 g of a desired product.

1-3) Synthesis of 4-amino-1-(4-carboxyphenyl)-2,3-dimethyl-5-pyrazolone methyl ester 2.0 g of 1-(4-carboxyphenyl)-2,3-dimethyl-5-pyrazolone methyl ester obtained in the above 1-2) was dissolved in 25 mL of 0.4N hydrochloric acid. To the resultant solution, 1.2 mL of a 40% aqueous solution of sodium nitrite (manufactured by KANTO CHEMICAL Co., Inc.: 37402-00) was added for 2 minutes while being chilled with ice, and sequentially stirred for 10 minutes at room temperature. A precipitated solid was collected by filtration, washed and dried. A solid was dissolved in 10 mL of methanol, and 2 mL of 4N hydrochloric acid and 1.1 g of zinc powder (manufactured by KANTO CHEMICAL Co., Inc.: 48005-00) were added. The resultant mixture was stirred for 10 minutes at 45° C. After filtering the reaction mixture, a filtrate was condensed to dryness, and subjected to silica gel chromatography using methanol/chloroform (1:9) as a solvent. A main fraction was condensed to dryness to yield 1.0 g of a desired product.

1-4) Synthesis of 4-amino-1-(4-carboxyphenyl)-2,3-dimethyl-5-pyrazolone 0.37 g of 4-amino-1-(4-carboxyphenyl)-2,3-dimethyl-5-pyrazolone methyl ester obtained in the above 1-3) was dissolved in 5 mL of methanol. To the resultant solution, 0.25 mL of an aqueous 4N sodium hydroxide solution was added, to carry out the reaction at room temperature for 30 minutes. After treating the reaction mixture by using strong cation exchange resin (manufactured by ALDRICH CHEMISTRY Co., Ltd.: 216534-250G), it was condensed to dryness to yield 0.25 g of a desired product.

NMR analysis results of the desired product obtained thereby are shown in the following Table 1.

Table 1
$^1$H-NMR (DMSO-$d_6$) 2.08 ppm (s, 3H, C—$CH_3$), 2.73 ppm (s, 3H, N—$CH_3$), 3.83 pm (br, 2H, $NH_2$), 7.29-7.94 ppm (4H, aromatic)

Example 2

Synthesis of 4-amino-1-(4-sulfophenyl)-2,3-dimethyl-5-pyrazolone (referred to as CP2)

2-1) Synthesis of 1-(4-sulfophenyl)-2,3-dimethyl-5-pyrazolone 3.0 g of 1-(4-sulfophenyl)-3-methyl-5-pyrazolone (manufactured by ALDRICH CHEMISTRY Co., Ltd.: 134163-25G), 3.4 g of methyl iodide (manufactured by KANTO CHEMICAL Co., Inc.: 10060), 100 mL of methanol were put in a high-pressure reactor, and stirred for 15 hours at 130° C. under heating. The reaction mixture was evaporated to dryness, and then recrystallized from ethanol to yield 1.4 g of a desired product.

2-2) Synthesis of 4-amino-1-(4-sulfophenyl)-2,3-dimethyl-5-pyrazolone 0.5 g of 1-(4-sulfophenyl)-2,3-dimethyl-5-pyrazolone obtained in the above 2-1) was dissolved in 10 mL of 0.4N hydrochloric acid. To the resultant solution, 0.35 mL of a 40% aqueous solution of sodium nitrite (manufactured by KANTO CHEMICAL Co., Inc.: 37402-00) was added while being chilled with ice, and stirred for 1 minute. 500 mg of zinc powder (manufactured by KANTO CHEMICAL Co., Inc.: 48005-00) was added thereto. The resultant mixture was stirred for 10 minutes at room temperature. After filtering the reaction mixture, a filtrate was condensed to dryness to yield 0.41 g of a desired product.

NMR analysis results of the desired product obtained thereby are shown in the following Table 2.

Table 2
$^1$H-NMR ($D_2O$) 2.27 ppm (s, 3H, C—$CH_3$), 3.15 ppm (s, 3H, N—$CH_3$), 7.44-7.99 ppm (4H, aromatic)

Example 3

Synthesis of 4-amino-1-(3-sulfophenyl)-2,3-dimethyl-5-pyrazolone (referred to as CP6)

3-1) synthesis of 1-(3-sulfophenyl)-3-methyl-5-pyrazolone

A mixture of 5.0 g of phenylhydrazine-3-sulfonic acid and 6.1 g of ethyl 3-oxobutanoate was stirred for 1 hour at 120° C. under heating. The reaction mixture was standing to cool. A precipitated solid was collected by filtration, washed, and dried to yield 8.0 g of a desired product.

3-2) Synthesis of 1-(3-sulfophenyl)-2,3-dimethyl-5-pyrazolone 3.0 g of 1-(3-sulfophenyl)-3-methyl-5-pyrazolone obtained in the above 3-1), 3.4 g of methyl iodide, and 100 mL of methanol were put in a high-pressure reactor, and stirred for 15 hours at 130° C. under heating. The reaction mixture was evaporated to dryness, and recrystallized from ethanol to yield 1.5 g of a desired product.

3-3) Synthesis of 4-amino-1-(3-sulfophenyl)-2,3-dimethyl-5-pyrazolone 0.5 g of 1-(3-sulfophenyl)-2,3-dimethyl-5-pyrazolone obtained in the above 3-2) was dissolved in 10 mL of 0.4N hydrochloric acid. To the resultant solution, 0.35 mL of an aqueous 40% sodium nitrite solution was added while being chilled with ice, and stirred for 1 minute, and 500 mg of zinc powder was added thereto. Further, the resultant mixture was stirred for 10 minutes at room temperature. The reaction mixture was filtrated, and a filtrate was condensed to dryness to yield 0.37 g of a desired product.

NMR analysis results of the desired product obtained thereby are shown in the following Table 3.

Table 3

$^1$H-NMR (D$_2$O) 2.24 ppm (s, 3H, C—CH$_3$), 3.11 ppm (s, 3H, N—CH$_3$), 7.35-8.21 ppm (4H, aromatic)

Example 4

As an example of a coating liquid composition for measuring glucose, an experiment was conducted to determine a maximum concentration of a coating liquid. Specifically, when amounts of all the reagents were gradually increased using the following basic composition in which kinds and amounts (to become an equimole amount of 4-aminoantipyrine) of each coupler were varied, how many times of the amount can be increased to obtain a uniform solution was observed. The results are shown in the following Table 4.

Basic Composition (in 100 mL Water)

1.0 g of a coupler compound (4-AA), 0.8 g of Trinder's reagent (TOOS), 5.0 g of Triton (registered trademark) X-100, 2.0 g of glucose oxidase, 0.5 g of peroxidase, 0.05 M of sodium citrate-citric acid (adjusted to give pH=5.0)

TABLE 4

| Coupler Compound | Solubility of coupler |
| --- | --- |
| 4-Aminoantipyrine | 5 times by volume |
| 4-Amino-1-(4-carboxyphenyl)-2,3-dimethyl-5-pyrazolone | 8 times by volume |
| 4-Amino-1-(4-sulphophenyl)-2,3-dimethyl-5-pyrazolone | 10 times by volume |
| 4-Amino-1-(3-sulphophenyl)-2,3-dimethyl-5-pyrazolone | 10 times by volume |

It can be noted from Table 4 that the compounds of the present invention (CP1, CP2 and CP6) all show high solubility, as compared with 4-aminoantipyrine which has been generally used as a coupler heretofore, indicating that a coating liquid with a high concentration can be prepared by using the compounds of the present invention.

Example 5

A test membrane having a composition in which only a coupler concentration was varied was prepared, and tested for its effects on glucose quantitative value. Specifically, a polyethersulfone membrane (manufactured by Terumo Corporation, membrane thickness of 130 μm) was coated with a coating liquid having the following composition, and dried for 18 hours at 35° C. The membrane was punched out to give a 1-cm square, and the square sample was placed in a reflectance spectrophotometer. Then, 1 μL of a specimen was added dropwise onto the test membrane from above. After 10 seconds, the reflection-absorbance was measured. As a specimen, human blood adjusted to 40 of hematocrit level and 100 mg/dL of blood glucose level was employed. The results are shown in FIG. 1.

Figure 1:
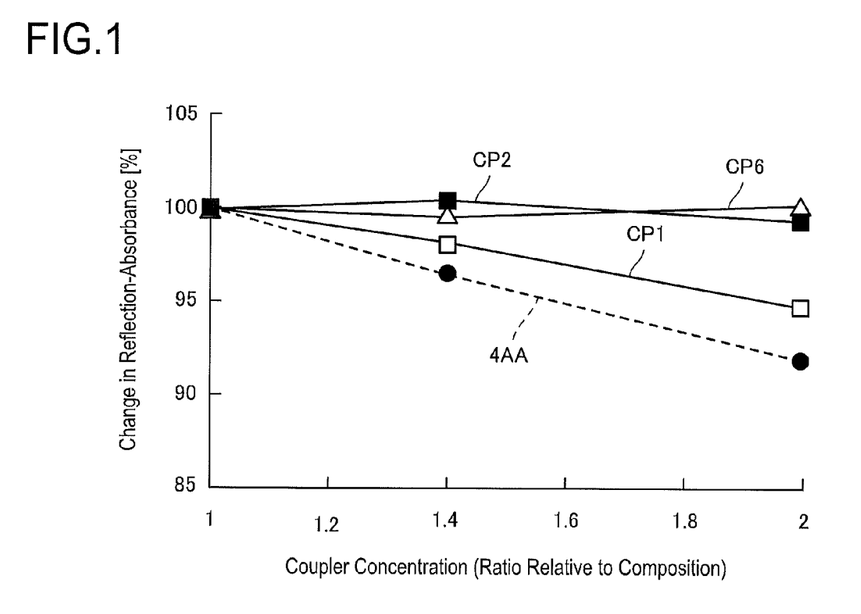
FIG. 1 is a graph showing a rate of change in reflection-absorbance with respect to a coupler concentration in Example 5 as mentioned below.

As shown in FIG. 1, it was observed that the compounds (CP1, CP2 and CP6) of the present invention all exhibited a decreased concentration dependence of sensitivity, as compared with 4-aminoantipyrine ("4AA" in the FIG. 1).

Coating Liquid Composition (in 100 mL of 0.1 M of Sodium Citrate-Citrate Buffer Solution (pH=5.0))

4.0 g/5.6 g/8.0 g of coupler compound, 3.2 g of Trinder's reagent (MAOS), 20.0 g of Triton (registered trademark) X-100, 8.0 g of glucose oxidase, and 2.0 g of peroxidase

Example 6

Figure 2:
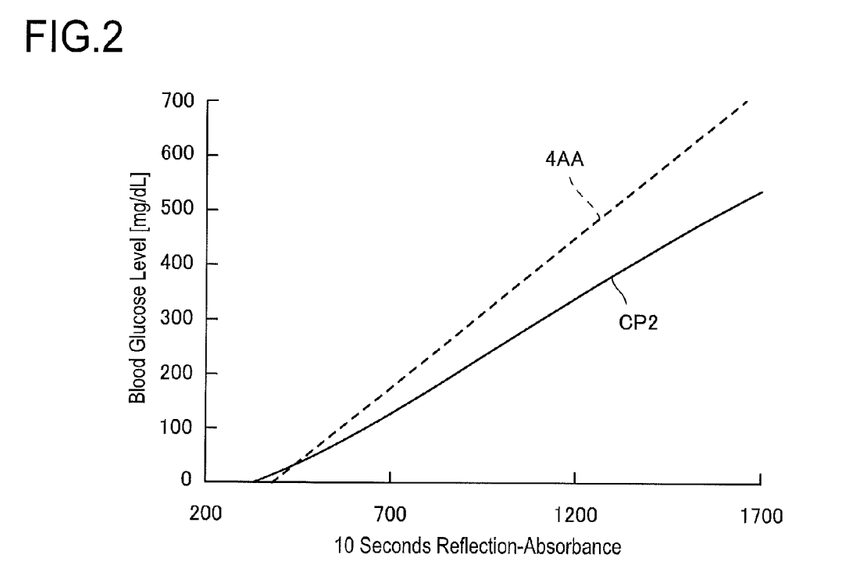
FIG. 2 is a graph showing a blood glucose level with respect to ten seconds reflection-absorbance in Example 6 as mentioned below.

Of the coupler concentrations used in the Example 5, a test membrane was prepared employing the same basic composition as for CP2. Using the test membrane, a standard curve was prepared from values measured at various known glucose concentrations, and quantitative sensitivity was observed. It should be noted that the evaluation method was the same as the method shown in the Example 5. The standard curves as the results are shown in FIG. 2. In FIG. 2, since X axis shows reflection-absorbance, and Y axis shows blood glucose level, indicating that lower slope means higher sensitivity.

As shown in FIG. 2, when 4-amino-1-(4-sulfophenyl)-2,3-dimethyl-5-pyrazolone (CP2) of the present invention was colored by combining with MAOS as Trinder's reagent, it is shown that the slope of the standard curve can be improved as compared with the case using 4-aminoantipyrine, and that the measurement sensitivity can be significantly enhanced.

Example 7

Using a coating liquid having a composition shown in the following Table 5, a polyether sulfone membrane (membrane thickness: 130 μm) manufactured by Terumo Corporation was coated by Kiss-Coat method, and dried for 18 hours at 37° C. Then, the membrane was cut to give a 1-cm square as a test piece.

TABLE 5

Coating Liquid Composition
(in 100 mL of 0.4M of sodium succinate buffer (pH = 5.0))

| | | Applied Amount of Reagent |
| --- | --- | --- |
| Coupler Compound | 15 mmol | 30.7 μmol/cm$^3$ |
| Trinder's Reagent (MAOS) | 15 mmol | 30.7 μmol/cm$^3$ |
| Triton X-100 | 13.0 g | 26.7 mg/cm$^3$ |
| Glucose Oxidase | 1300 kU | 2.7 U/cm$^3$ |
| Peroxidase | 1000 kU | 2.1 U/cm$^3$ |

The evaluation using blood was conducted by fixing the test piece in a reflectance spectrophotometer, adding 1 μL of specimen dropwise onto the test membrane from above, and measuring reflection-absorbance continuously or at the predetermined time.

Figure 3:
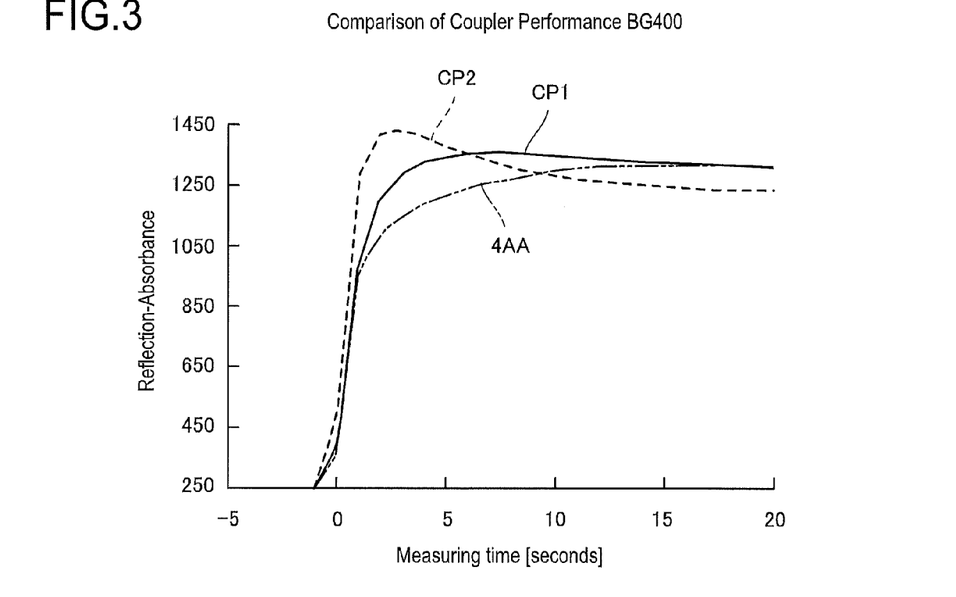
FIG. 3 is a graph showing change in reflection-absorbance over time in Example 7 as mentioned below.

The time-dependent changes in the reflection-absorbance was measured using as a coupler compound 4-amino antyprine (4-AA), CP1 or CP2, the test piece prepared by the above method, and human blood adjusted to 40% of hematocrit level and 400 mg/dL of blood glucose level as specimen. The results are shown in FIG. 3. It is noted from the results shown in FIG. 3 that 15 seconds was required for reflection-absorbance to become steady when using 4-AA, a conventional coupler, while less than 5 seconds was required for reflection-absorbance to become steady when using CP1, and particularly when using CP2, reflection-absorbance reached peak within only about 3 seconds. That is, it was observed that a measuring time was able to be shortened by using the reagent composition of the present invention.

Example 8

Figure 4:
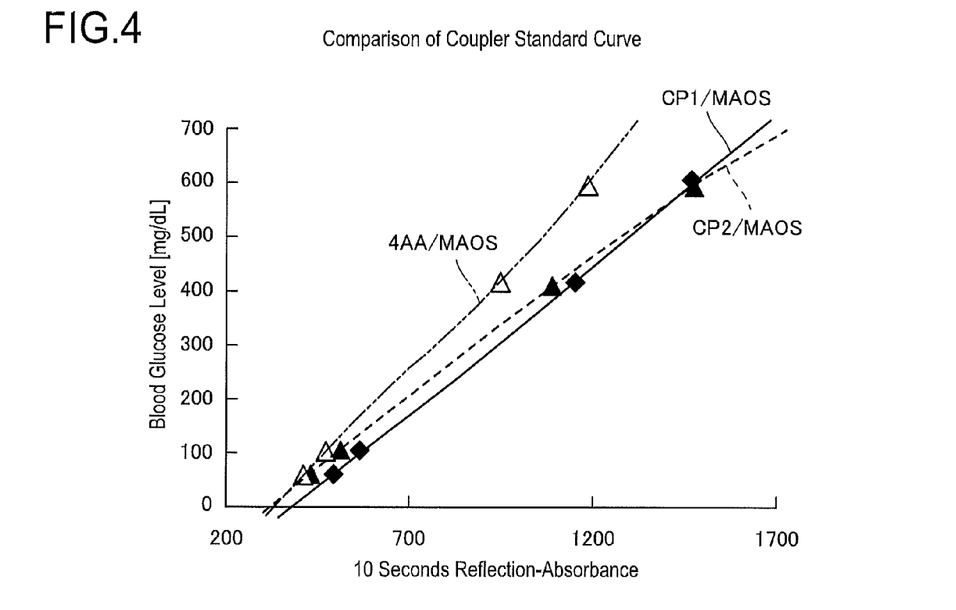
FIG. 4 is a graph showing a standard curve made on the basis of reflection-absorbance in case of changing a blood glucose concentration in Example 8 as mentioned below.

A standard curve was made from the reflection-absorbance obtained by using the test piece prepared in the Example 7, and human blood adjusted to 40% of hematocrit level and 50, 100, 400, and 600 mg/dL of blood glucose levels as specimen. Measured sensitivities were compared. The results are shown in FIG. 4. In this figure, Y axis (longitudinal axis) shows blood glucose level (input value) and X axis (horizontal axis) shows reflection-absorbance (output value), indicating that lower slope means higher sensitivity. It is noted from the results shown in FIG. 4 that the slopes of the standard curves when using CP1 and CP2 decrease as compared with that of 4-AA. That is, it was observed that measurement sensitivity can be improved by using the reagent composition of the present invention.

Example 9

Using a coating liquid having a composition shown in the following Table 6, a polyether sulfone membrane (membrane thickness: 130 μm) manufactured by Terumo Corporation was coated by Kiss-Coat method, and dried for 18 hours at 37° C. Then, the membrane was punched out to give a circle of φ6 mm as a test piece.

TABLE 6

Coating Liquid Composition
(in 100 mL of 0.4M of monosodium succinate buffer (pH = 5.0))

|  |  | Applied Amount of Reagent |
|---|---|---|
| Coupler Compound | 15 mmol | 30.7 μmol/cm$^3$ |
| Trinder's Reagent (MAOS) | 15 mmol | 30.7 μmol/cm$^3$ |
| Triton X-100 | 13.0 g | 26.7 mg/cm$^3$ |
| Glucose Oxidase | 1900 kU | 3.9 U/cm$^3$ |
| Peroxidase | 1000 kU | 2.1 U/cm$^3$ |

Figure 5:
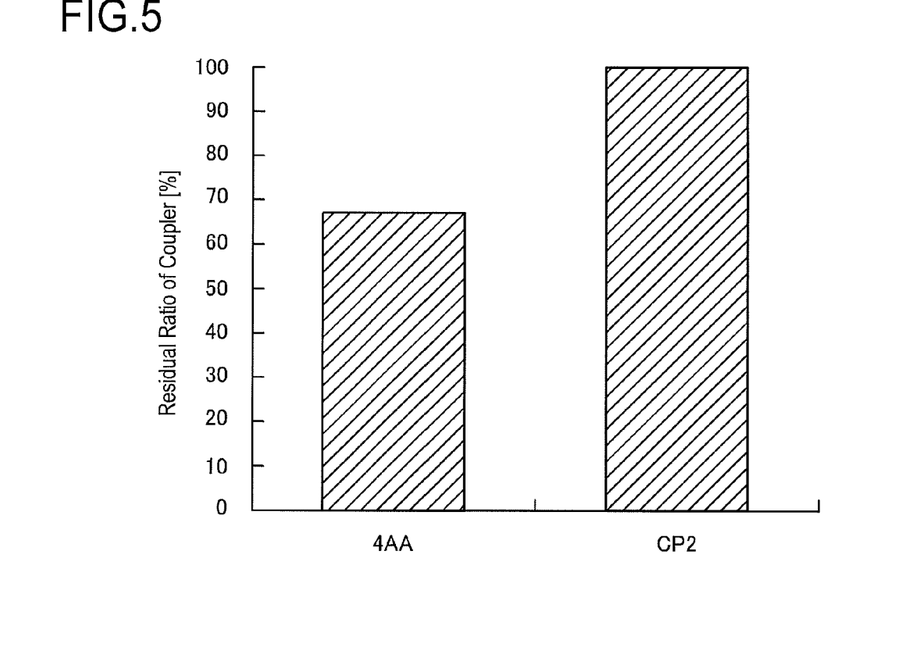
FIG. 5 is a graph showing a residual rate of 4-AA and CP2 included in a test piece after heat acceleration in Example 9 as mentioned below.

The test piece was placed in an oven under vacuum at 60° C. for 1 hour to be subjected to thermal acceleration. Then, the test piece was subjected to ultrasonic treatment for 10 minutes using 1 ml of an aqueous 60% acetonitrile solution, and extracted. The amount of reagent in the resultant extract was determined by HPLC under such conditions as of eluent: 60% of acetonitrile/50 mM of phosphate buffer (pH 7.5), eluent flow rate: 1 mL/minute, column temperature: 40° C., column: Hydrosphere C18 250×4.6 mm (manufactured by YMC Co., Ltd.), measuring wavelength: 254 nm, and injection volume: 20 μL. According to this method, the residual ratios of 4-AA and CP2 contained in the test piece after thermal acceleration were respectively compared with those of the test pieces before thermal acceleration. The results are shown in FIG. 5. It is noted from the results shown in FIG. 5 that the residual ratio of 4-AA is not more than 70%, while the residual ratio of CP2 is approximately 100%. That is, it is shown that the stability over time of the test instrument can be improved by using the reagent composition of the present invention.

Example 10

Using coating liquids which compositions shown in the following Table 7 are arranged in accordance with L18 orthogonal layout (nine factors, and three levels), a polyether sulfone membrane (membrane thickness: 130 μm) manufactured by Terumo Corporation was coated by Kiss-Coat method, and dried for 18 hours at 37° C. Then, the membrane was cut to give a 1-cm square as a test piece.

TABLE 7

Coating Liquid Composition (in 100 mL of buffer)

|  |  | Applied Amount of Reagent |
|---|---|---|
| Coupler compound (CP2) | 5 to 15 mmol | 10.3-30.8 μmol/cm$^3$ |
| Trinder's reagent (MAOS) | 5 to 15 mmol | 10.3-30.8 μmol/cm$^3$ |
| pH of Buffer | 5.0 to 6.0 | — |
| Buffer | Succinic acid, Citric acid, Acetic acid | — |
| Solubilizer | 13.0 g | 26.7 mg/cm$^3$ |
| Glucose oxidase | 1300 kU | 2.7 U/cm$^3$ |
| Peroxidase | 500 kU | 1.0 U/cm$^3$ |
| Buffer Concentration | 400 mM | 76.9 μmol/cm$^3$ |

The evaluation using blood was conducted by fixing the test piece in a reflectance spectrophotometer, adding 1 μL of specimen dropwise onto the test membrane from above, and measuring reflection-absorbance continuously or at the predetermined time.

Figure 6:
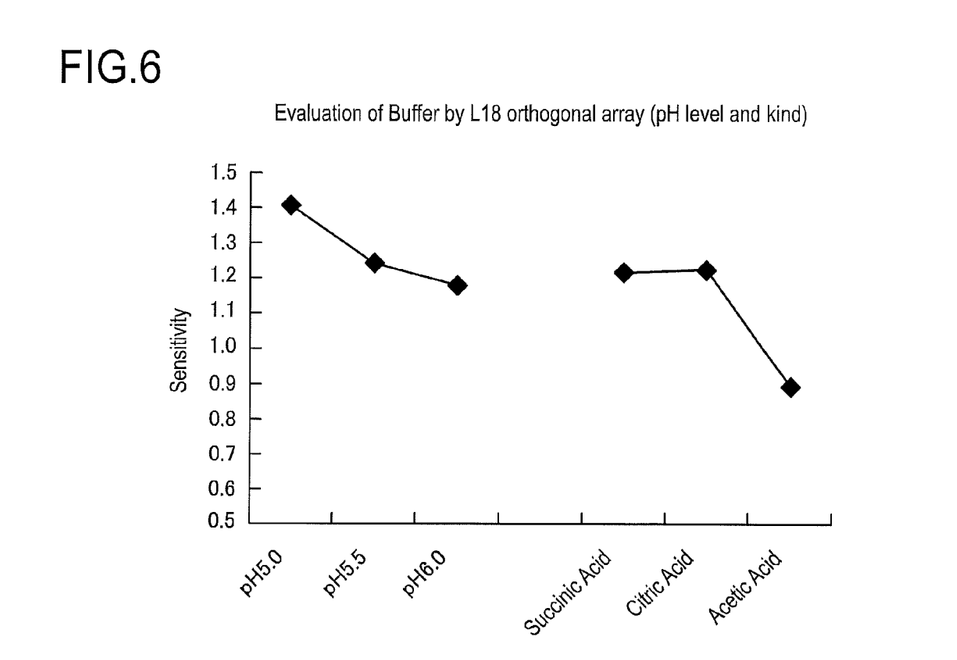
FIG. 6 is a graph showing measured results of change in measurement sensitivity with respect to varied pH and type of a pH buffer from a L18 orthogonal array in Example 10 as mentioned below.

For each the test piece, a standard curve was made from reflection-absorbance obtained by using human blood adjusted to 40% of hematocrit level and 50, 100, 400, and 600 mg/dL of blood glucose levels as specimen, to calculate measurement sensitivities. Among 18 combinations, measurement sensitivities were calculated for each of pH of the pH buffer and kinds of pH buffers, and compared each other. The results are shown in FIG. 6. It is noted from the results shown in FIG. 6 that lower pH of pH buffer could attain improved measurement sensitivity, and succinic acid and citric acid are suitable as a pH buffer.

Example 11

Using a coating liquid having a composition shown in the following Table 8, a polyether sulfone membrane (membrane thickness: 130 μm) manufactured by Terumo Corporation was coated by Kiss-Coat method, and dried for 18 hours at 37° C. Then, the membrane was cut to give a 1-cm square as a test piece.

TABLE 8

Coating Liquid Composition
(in 100 mL of 0.4M of monosodium succinate buffer (pH = 5.0))

|  |  | Applied Amount of Reagent |
|---|---|---|
| Coupler Compound | 10 mmol | 20.5 μmol/cm$^3$ |
| Trinder's Reagent (MAOS) | 10 mmol | 20.5 μmol/cm$^3$ |
| Triton X-100 | 13.0 g | 26.7 mg/cm$^3$ |
| Glucose Oxidase | 1300 kU | 2.7 U/cm$^3$ |
| Peroxidase | 500 kU | 1.0 U/cm$^3$ |

The evaluation using blood was conducted by fixing the test piece in a reflectance spectrophotometer, adding 1 μL of specimen dropwise onto the test membrane from above, and measuring reflection-absorbance continuously or at the predetermined time.

Figure 7:
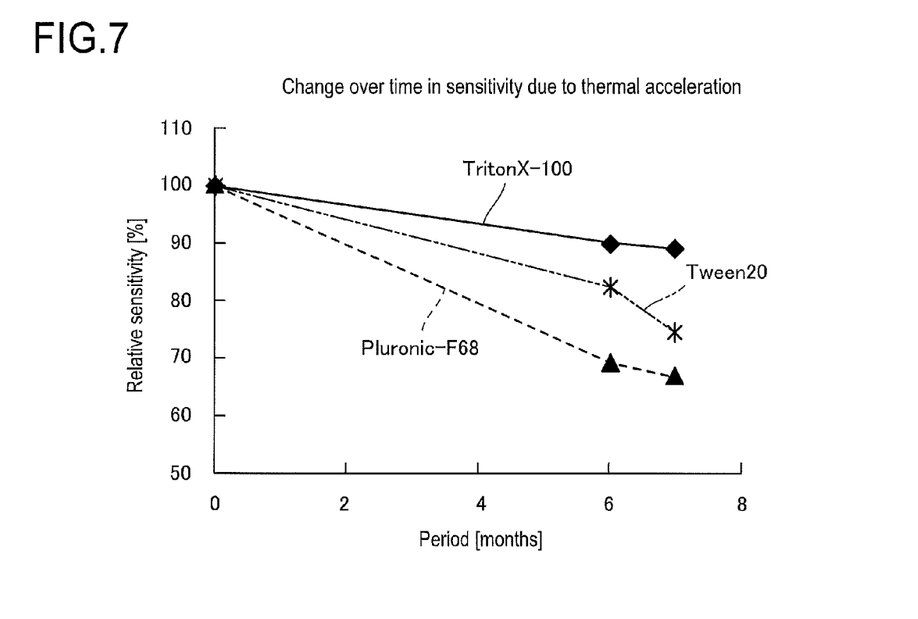
FIG. 7 is a graph showing measured results of temporal change in relative sensitivity by varying a kind of solubilizer in Example 11 as mentioned below.

The test piece prepared by the above method using Triton (registered trademark) X-100, Tween 20, Pluronic-F68 as a solubilizer was placed at 60° C. for a prescribed period in a shading and dry state (thermal acceleration test). The test piece placed for a prescribed period was tested for a relative sensitivity using human blood adjusted to 40 of hematocrit level and 400 mg/dL of blood glucose level as specimen, and time-dependent change in the relative sensitivity is shown in FIG. 7. It is noted from the results shown in FIG. 7 that among three solubilizers, Triton (registered trademark) X-100 shows the smallest reduction of relative sensitivity and thus is most excellent in stability over time.

Example 12

Figure 8:
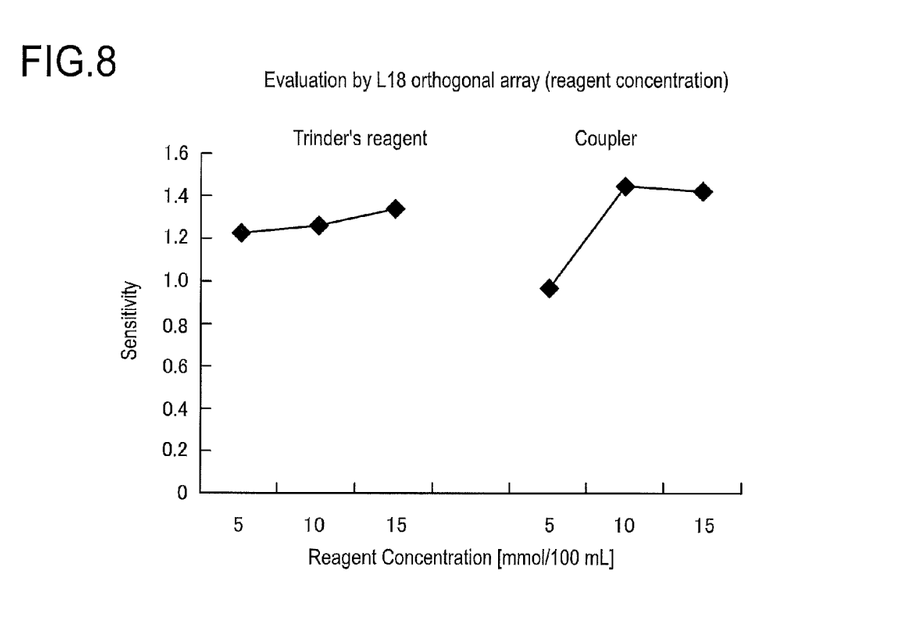
FIG. 8 is a graph showing measured results of change in measurement sensitivity with respect to changes in concentration of a coupler compound and concentration of Trinder's reagent in Example 12 as mentioned below.

A standard curve was made from the reflection-absorbance obtained by using the test piece prepared in the Example 10, and human blood adjusted to 40% of hematocrit level and 50, 100, 400, and 600 mg/dL of blood glucose levels as specimen. And measurement sensitivities were calculated. Among 18 combinations, measurement sensitivities were calculated for each of concentration of a coupler compound and concentration of Trinder's reagent, and compared each other. The results are shown in FIG. 8. It is noted from the results shown in FIG. 8 that 5 mmol/100 mL as the concentration of coupler compound showed significantly lower measurement sensitivity as compared with that of 10 mmol/100 mL, and the concentration of 10 mmol/100 mL or more showed stable measurement sensitivity, indicating that the minimum concentration of the coupler compound is 10 mmol/100 mL or more. In addition, it is also noted that Trinder's reagent shows stable measurement sensitivity within concentration range shown therein, indicating that the concentration of Trinder's reagent can be set in accordance with the concentration of coupler as a coupling partner.

The entire disclosure of Japanese Patent Application No. 2007-72807 filed on Mar. 20, 2007 and Japanese Patent Application No. 2007-254475 filed on Sep. 28, 2007 including specification, claims, drawings and summary are incorporated herein by reference in its entirety.

The invention claimed is:

1. An oxidative chromogenic compound or salt thereof represented by the following chemical formula (1):

[Formula 1]

(1)

wherein $R^1$ and $R^2$ are each independently a linear or branched C1-C5 alkyl group;

$R^3$, $R^4$, $R^5$, $R^6$ and $R^7$ are each independently a hydrogen atom, a carboxyl group or a sulfonic acid group, or salt thereof, provided that at least one of $R^3$ to $R^7$ is a carboxyl group or a sulfonic acid group, or salt thereof, and the others are hydrogen atoms.

2. The oxidative chromogenic compound or salt thereof according to claim 1, wherein in the formula (1), $R^1$ and $R^2$ are each a methyl group.

3. The oxidative chromogenic compound or salt thereof according to claim 1, wherein in the formula (1), $R^5$ is a carboxyl group or a sulfonic acid group, or salt thereof, and $R^3$, $R^4$, $R^6$ and $R^7$ are a hydrogen atom.

4. The oxidative chromogenic compound or salt thereof according to claim 1, wherein in the formula (1), $R^4$ is a carboxyl group or a sulfonic acid group, or salt thereof, and $R^3$, $R^5$, $R^6$ and $R^7$ are a hydrogen atom.

5. The oxidative chromogenic compound or salt thereof according to claim 1, wherein in the formula (1), $R^4$ and $R^6$ are each a carboxyl group or a sulfonic acid group, or salt thereof, and $R^3$, $R^5$ and $R^7$ are a hydrogen atom.

6. A reagent composition comprising the oxidative chromogenic compound or salt thereof set forth in claim 1, a Trinder's reagent, oxidase, and peroxidase.

7. The reagent composition according to claim 6, wherein said Trinder's reagent is one or more members selected from the group consisting of:
N-ethyl-N-(3-sulfopropyl)-3-methylaniline;
N-ethyl-N-(3-methylphenyl)-3-acetylethylenediamine;
N-ethyl-N-(3-methylphenyl)-N-succinylethylenediamine;
N-ethyl-N-(2-hydroxy-3-sulfopropyl)-3-methylaniline;
N-(2-carboxyethyl)-N-ethyl-3-methylaniline;
N,N-bis-(4-sulfobutyl)-3-methylaniline;
N-ethyl-N-(2-succinylaminoethyl)-3-methylaniline;
N-ethyl-N-(3-sulfopropyl)-3-methoxyaniline;
N-(2-hydroxy-3-sulfopropyl)-3,5-dimethoxyaniline;
N-ethyl-N-(2-hydroxy-3-sulfopropyl)-3,5-dimethoxyaniline;
N-ethyl-N-(2-hydroxy-3-sulfopropyl)-3,5-dimethoxy-4-fluoroaniline; and
N-ethyl-N-(2-hydroxy-3-sulfopropyl)-3,5-dimethylaniline.

8. The reagent composition according to claim 6, which further comprises a pH buffer or a solubilizer.

9. The reagent composition according to claim 8, wherein said pH buffer is an organic acid salt.

10. The reagent composition according to claim 9, wherein said organic acid salt is an organic carboxylic acid salt.

11. The reagent composition according to claim 10, wherein said organic carboxylic acid salt is a salt of one or more acids selected from the group consisting of acetic acid, propionic acid, butyric acid, fumaric acid, maleic acid, phthalic acid, succinic acid, malonic acid, citric acid and malic acid.

12. The reagent composition according to claim 8, wherein the pH of said pH buffer is in the range of 4.0 to 6.0.

13. The reagent composition according to claim 8, wherein said solubilizer is one or more members selected from the group consisting of carboxymethylcellulose, polyethylene glycol, polyoxyethylene-p-t-octylphenol, sorbitan alkylate, sorbitan polyoxyethylene ether, polyoxylene-ethyleneoxyl block polymer, polyoxyethylene nonylphenol, and polyoxyethylene-n-alkyl ether.

14. The reagent composition according to claim 6, wherein the molar ratio of contents of the oxidative chromogenic compound or salt thereof and the Trinder's reagent is 1:1 to 2:1.

15. The reagent composition according to claim 6, wherein said oxidase is glucose oxidase.

16. An instrument for colorimetric testing having the reagent composition set forth in claim 6 supported on a carrier.

17. The instrument according to claim 16, wherein said carrier is a polymeric membrane.

18. The instrument according to claim 17, wherein the polymeric membrane is constituted of polysulfone or polyether sulfone.

19. The instrument according to claim 16, wherein the content of the oxidative chromogenic compound or salt thereof is in the range of 15 to 62 μmol, the content of the Trinder's reagent is in the range of 7.5 to 62 μmol, the content of the pH buffer is in the range of 40 to 155 μmol, and the content of the solubilizer is in the range of 19 to 45 mg, per 1cm³ of the carrier.

20. A process for the production of the oxidative chromogenic compound or salt thereof set forth in claim 1, which comprises reacting a compound represented by the following chemical formula (2):

[Formula 2]

(2)

wherein $R^1$ is a linear or branched alkyl group having 1 to 5 carbon atoms, with a compound represented by the following chemical formula (3):

[Formula 3]

(3)

wherein $R^3$, $R^4$, $R^5$, $R^6$ and $R^7$ are each independently a hydrogen atom, a carboxyl group or a sulfonic acid group, or salt thereof, provided that at least one of $R^3$ to $R^7$ is a carboxyl group or a sulfonic acid group, or salt thereof, and the others are hydrogen atoms.

21. A process for the production of the oxidative chromogenic compound or salt thereof set forth in claim 1, which comprises preparing as a starting material a compound represented by the following chemical formula (4):

[Formula 4]

(4)

wherein $R^1$ and $R^2$ are each independently a linear or branched alkyl group having 1 to 5 carbon atoms;

wherein $R^3$, $R^4$, $R^5$, $R^6$ and $R^7$ are each independently a hydrogen atom, a carboxyl group or a sulfonic acid group, or salt thereof, provided that at least one of $R^3$ to $R^7$ is a carboxyl group or a sulfonic acid group, or salt thereof, and the others are hydrogen atoms, and subjecting the compound to a nitrosation reaction followed by reduction.

* * * * *